(12) United States Patent
Lehmann et al.

(10) Patent No.: US 9,221,815 B2
(45) Date of Patent: Dec. 29, 2015

(54) SOLID STATE FORM OF VEMURAFENIB CHOLINE SALT

(71) Applicant: ratiopharm GmbH, Ulm (DE)

(72) Inventors: Frank Lehmann, Ulm (DE); Wolfgang Albrecht, Ulm (DE); Richard Guserle, Kotz (DE); Roland Selig, Ulm (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 14/412,039

(22) PCT Filed: Jul. 2, 2013

(86) PCT No.: PCT/US2013/049082
§ 371 (c)(1),
(2) Date: Dec. 30, 2014

(87) PCT Pub. No.: WO2014/008270
PCT Pub. Date: Jan. 9, 2014

(65) Prior Publication Data
US 2015/0183779 A1 Jul. 2, 2015

Related U.S. Application Data

(60) Provisional application No. 61/667,769, filed on Jul. 3, 2012.

(51) Int. Cl.
C07D 471/04 (2006.01)
C07C 215/40 (2006.01)

(52) U.S. Cl.
CPC ............ C07D 471/04 (2013.01); C07C 215/40 (2013.01)

(58) Field of Classification Search
CPC ..................... A61K 31/437; C07D 471/04
See application file for complete search history.

(56) References Cited

U.S. PATENT DOCUMENTS 7,863,288 B2    1/2011   Ibrahim et al.

FOREIGN PATENT DOCUMENTS

WO          2010114928     * 10/2010
WO          2010129570     * 11/2010
WO       WO 2011/057974      5/2011
WO          2012161776     * 11/2012

OTHER PUBLICATIONS

Salt Selection for basic drugs, Phillip Gould 1986.*
Pharmaceutical salts, Stephen Berge, 1977.*

* cited by examiner

Primary Examiner — Rita Desai
(74) Attorney, Agent, or Firm — Baker & Hostetler LLP

(57) ABSTRACT

The present invention relates to Vemurafenib choline salt, solid state forms thereof, processes for preparation thereof and formulations thereof. The present invention also relates to the use of the solid state forms of Vemurafenib choline salt for preparing Vemurafenib or other Vemurafenib salts, and solid state forms thereof. Vemurafenib has the following chemical structure:

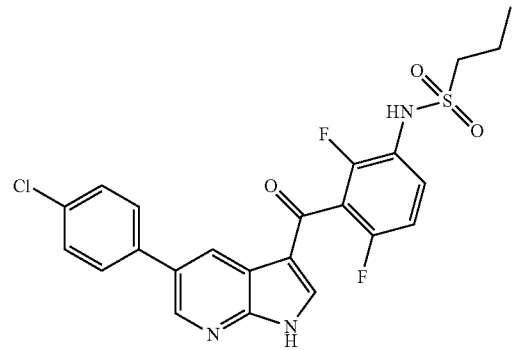

9 Claims, 16 Drawing Sheets

SOLID STATE FORM OF VEMURAFENIB CHOLINE SALT

CROSS-REFERENCE TO RELATED APPLICATIONS

This application is the National Stage of International Application No. PCT/US2013/049082, filed Jul. 2, 2013, which claims the benefit of priority of U.S. Provisional Application No. 61/667,769, filed Jul. 3, 2012, the entire disclosures of which are incorporated herein by reference.

FIELD OF THE INVENTION

The present invention relates to Vemurafenib choline and esylate salts, solid state forms thereof, processes for preparation thereof and formulations thereof.

The present invention also relates to solid state forms of Vemurafenib, processes for preparation thereof, formulations thereof, and the conversion of the solid state forms to Vemurafenib salts.

BACKGROUND OF THE INVENTION

Vemurafenib, propane-1-sulfonic acid {3-[5-(4-chlorophenyl)-1H-pyrrolo[2,3-b]pyridine-3-carbonyl]-2,4-difluoro-phenyl}-amide, has the following chemical structure:

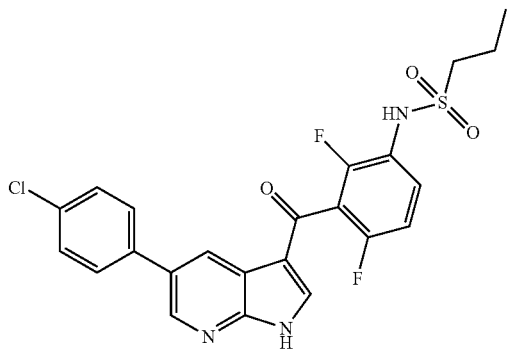 [SMILES: CCCS(=O)(=O)Nc1ccc(F)c(C(=O)c2c[nH]c3ncc(-c4ccc(Cl)cc4)cc23)c1F]

Vemurafenib is a BRAF kinase inhibitor, which is marketed under the trade name ZELBORAF® for the treatment of patients with metastatic melanoma with the BRAF V600E mutation. Vemurafenib tablets contains 240 mg of vemurafenib as a co-precipitate of vemurafenib and hypromellose acetate succinate (HPMCAS).

U.S. Pat. No. 7,863,288 discloses Vemurafenib. WO 2010/114928 discloses crystalline forms I and II of Vemurafenib; its mesylate, tosylate, maleate, oxalate, dichloroacetate salts, as well as solid dispersions that include Vemurafenib and a ionic polymer, in a ratio of Vemurafenib and the ionic polymer of about 1:9 to about 5:5, preferably about 3:7 (by weight). WO 2010/129570 discloses non-crystalline complexes of Vemurafenib and its L-arginine and L-lysine salts. WO 2011/057974 describes a solid dispersion of Vemurafenib, and describes that the amorphous form of Vemurafenib has improved solubility in water as compared to the crystalline form, but it is unstable. WO 2012/161776 discloses additional solid forms and salts of Vemurafenib, including a hydrochloride salt.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Polymorphism, the occurrence of different crystal forms, is a property of some molecules and molecular complexes. A single compound, like Vemurafenib, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C—)NMR spectrum. One or more of these techniques may be used to distinguish different polymorphic forms of a compound.

Discovering new salts and polymorphic forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional salts and solid state forms (including solvated forms) of vemurafenib.

SUMMARY OF THE INVENTION

The present invention provides Vemurafenib salts, particularly Vemurafenib esylate and Vemurafenib choline, and solid state forms thereof; and processes for preparing these compounds. The present invention also provides the use of the solid state forms of Vemurafenib and of the Vemurafenib salts for preparing Vemurafenib or other Vemurafenib salts, and solid state forms thereof.

The present invention provides Vemurafenib esylate and choline salts, solid state forms thereof, pharmaceutical compositions and formulations comprising at least one, or a combination, of the solid state forms of Vemurafenib esylate and choline salts and processes for preparation thereof.

The present invention also provides the use of Vemurafenib esylate and choline and their solid state forms; as well as solid state fauns of Vemurafenib for preparing pharmaceutical compositions and formulations. The present invention further provides pharmaceutical compositions comprising any one of, or a mixture of the solid state forms of Vemurafenib or the Vemurafenib esylate and choline salts and its solid state forms according to the present invention. The pharmaceutical compositions may additionally comprise at least one pharmaceutically acceptable excipient, thereby yielding pharmaceutical formulations.

The invention further provides a process for preparing formulations of Vemurafenib and Vemurafenib salts comprising combining any one or a mixture of the salts or solid state forms of the present invention and at least one pharmaceutically acceptable excipient.

Any of the solid state forms of Vemurafenib; Vemurafenib esylate, or Vemurafenib choline and their solid state forms as defined herein as well as the pharmaceutical compositions and formulations of vemurafenib can be used as medicaments, particularly for the treatment of cancer.

The present invention also provides a method of treating patients with cancer by administering a therapeutically effective amount of a pharmaceutical composition comprising at least one, or a combination, of the solid state forms of Vemurafenib; Vemurafenib esylate, or Vemurafenib choline and their solid state forms thereof; of the present invention, and optionally at least one pharmaceutically acceptable excipient to a patient in need thereof. The present invention also provides a method of treating patients with cancer by administering a pharmaceutical composition comprising a therapeutically effective amount of at least one, or a combination, of the solid state forms of Vemurafenib; Vemurafenib esylate or Vemurafenib choline and their solid state forms; of the present invention and optionally at least one pharmaceutically acceptable excipient to a patient in need thereof.

The present invention also provides the use of the Vemurafenib salts and solid state forms thereof of the present invention, or at least one of the above pharmaceutical compositions and formulations for the manufacture of a medicament for treating cancer.

DETAILED DESCRIPTION OF THE INVENTION

Figure 1:
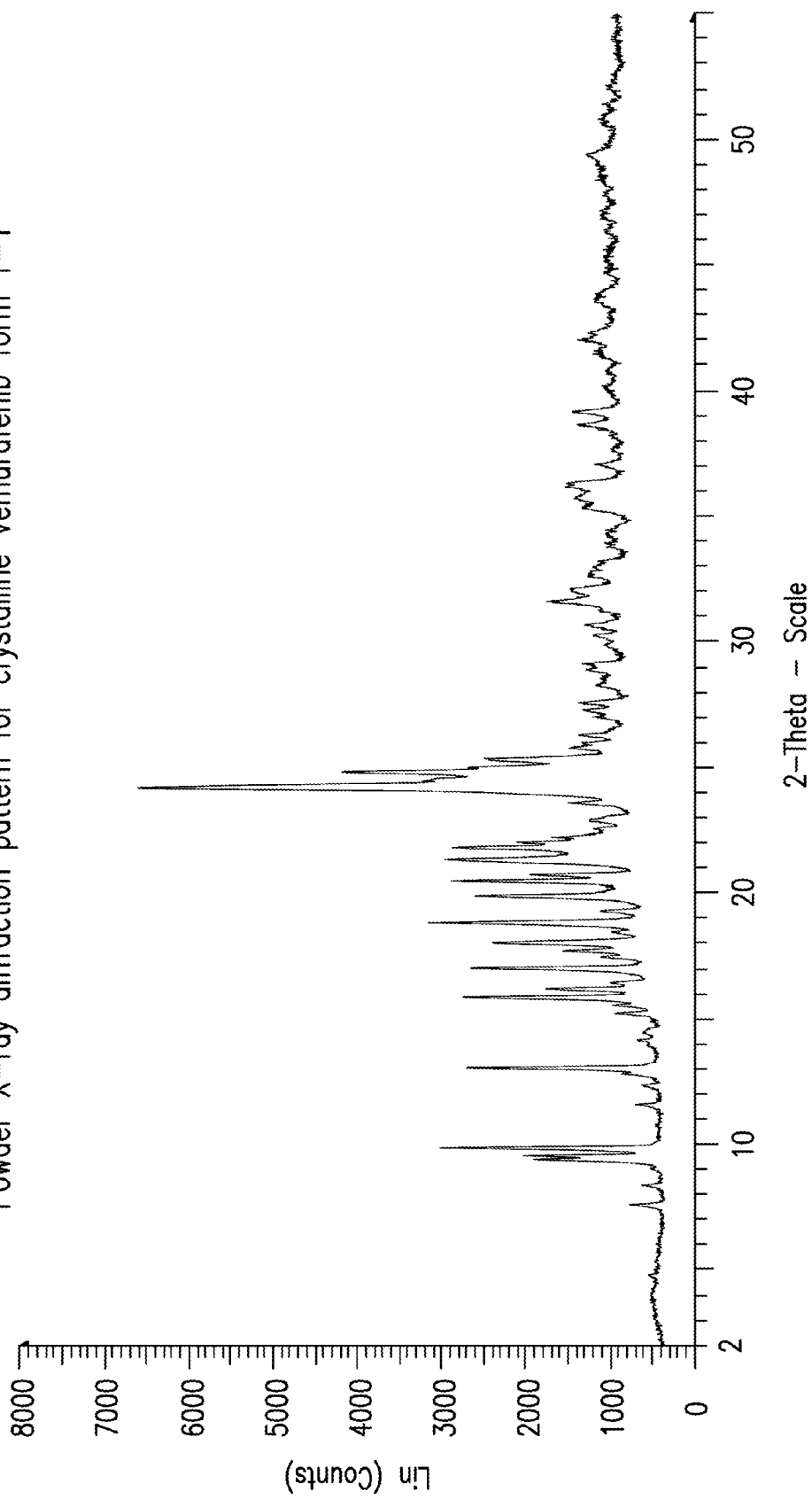
FIG. 1 shows a powder X-ray diffraction pattern ("Powder XRD" or "PXRD") for crystalline Vemurafenib form T-1.

The present invention relates to Vemurafenib salts, such as the esylate and choline salts, to solid state forms of these salts, to processes for preparation thereof and to pharmaceutical compositions and formulations comprising at least one, or a combination of these salts. The present invention also relates to solid state forms of Vemurafenib, to processes for preparation thereof, to pharmaceutical compositions and formulations comprising at least one, or a combination, of these solid state forms. The invention also relates to the conversion of the Vemurafenib salts and its solid state forms to Vemurafenib or other Vemurafenib salts.

In accordance with WO 2010/114928 and WO 2010/129570, it was observed that Vemurafenib has an extremely low solubility which makes it difficult to formulate and may result in poor bioavailability.

Amorphous Vemurafenib may improve solubility, however it is not stable.

WO 2010/129570 also states that other base-addition salts, such as the sodium and potassium salts are difficult to isolate and hygroscopic. In addition, it was found that those salts also contain large amounts of residual solvent. Attempts to develop stable, solvent-free and robust crystalline form of such salts were not successful. The Vemurafenib arginine and lysine complexes described in WO 2010/129570 are stated to be non-crystalline complexes. However, their PXRD pattern shows some degree of crystallinity.

Consistent with the latter, it was found that the conversion of Vemurafinib free base to acid addition or base addition salts was in many cases not possible, rather leading to precipitation of the free base, or yielding non-crystalline complexes of the free base and the respective acid or base. For example, it was observed that a conversion into a variety of amine salts of vemurafenib could not be accomplished.

The present invention offers, amongst other things, Vemurafenib choline salt, particularly in a highly crystalline state, which can be in anhydrous form. The highly crystalline Vemurafenib choline has an improved solubility and has high chemical and crystalline purities which makes it suitable as a pharmaceutically acceptable salt. The crystalline Vemurafenib choline can be directly used to prepare highly soluble formulations, without the need of a solid dispersion formulation comprising the active ingredient in amorphous form. The latter is less economical and burdened with potential re-crystallization of the active ingredient, making quality control of solid dispersions more demanding as even a partial re-crystallization, which may have a substantial impact on dissolution properties of the drug substance and thus clinical efficacy, must be controlled.

The salts and solid state forms of the present invention may have advantageous properties selected from at least one of: chemical purity, flowability, solubility, morphology or crystal habit, stability—such as storage stability, stability to dehydration, and stability to polymorphic conversion, low hygroscopicity, and low content of residual solvents.

Particularly, the salts of the present invention can, inter alia, be used as intermediates that can be purified to provide pure Vemurafenib.

A crystal form may be referred to herein as being characterized by graphical data substantially "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Vemurafenib salt referred to herein as being characterized by graphical data "as depicted in" a Figure will thus be understood to include any crystal forms of the Vemurafenib salt characterized with the graphical data having such small variations in comparison with the Figure, as is well known to the skilled person.

A crystal form (or polymorph) may be referred to herein as substantially free of any other crystalline (or polymorphic) forms. As used herein in this context, the expression "substantially free of any other forms" will be understood to mean that the crystalline form contains 20% or less, 10% less, 5% or less, 2% or less, or 1% or less of any other forms of the subject compound as measured, for example, by PXRD. Thus, polymorphs of Vemurafenib or its salts that are described herein as substantially free of any other polymorphic forms would be understood to contain greater than 80% (w/w), greater than 90% (w/w), greater than 95% (w/w), greater than 98% (w/w), or greater than 99% (w/w) of the respective subject polymorphic form. Accordingly, in some embodiments of the invention, the described polymorphs of Vemurafenib or its salts may contain from 1% to 20% (w/w), from 5% to 20% (w/w), or from 5% to 10% (w/w) of one or more other crystal forms of the compound.

As used herein, unless stated otherwise, PXRD peaks reported herein are preferably measured using $CuK_\alpha$ radiation, $\lambda=1.5418$ Å.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located.

As used herein, the expression "room temperature" refers to a temperature between about 20° C. and about 30° C. or about 22° C. to about 27° C., or about 25° C. Usually, room temperature ranges from about 20° C. to about 25° C.

A process or step may be referred to herein as being carried out "overnight." This refers to a time interval, e.g., for the process or step, that spans the time during the night, when that process or step may not be actively observed. As used herein, the term "overnight" refers to a period of between about 8 hours and about 20 hours, or about 10 hours to about 18 hours. The period can also refer to 15 hours and about 20 hours, typically between about 16 to about 20 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, and unless stated otherwise, the term "anhydrous" in relation to crystalline Vemurafenib or Vemurafenib salts, such as Vemurafenib choline form C1, relates to a crystalline Vemurafenib which does not include any crystalline water (or other solvents) in a defined, stoichiometric amount within the crystal. Moreover, an "anhydrous" form contains not more than 2% (w/w) of either water or organic solvents as measured by TGA or by NMR.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein the term non-hygroscopic in relation to crystalline Vemurafenib refers to less than 0.2% (w/w) absorption of water, by the crystalline Vemurafenib as determined for example by TGA. Water can be for example atmospheric water.

As used herein, the term "isolated" in reference to Vemurafenib or Vemurafenib salt or solid state forms thereof of the present invention corresponds to Vemurafenib salt or solid state form thereof that is physically separated from the reaction mixture in which it is formed.

As used herein, the term "reduced pressure" refers to a pressure of about 10 mbar to about 50 mbar.

As used herein, and unless indicated otherwise, the term "thermo-dynamical stability" in relation to crystalline Vemurafenib or a Vemurafenib salt refers to resistance of the crystal to polymorphic conversion under certain conditions, for example, heating, melting or dissolving. In some embodiments, the term refers to less than 20%, 10%, 5%, 1%, or 0.5% (w/w) conversion of crystalline Vemurafenib or a Vemurafenib salt form to any other solid state form of Vemurafenib or a Vemurafenib salt. In some embodiments, the conversion is 1%-20%, 1%-10% or 1%-5% (w/w).

The present invention also encompasses a Vemurafenib tetrahydrofuran ("THF") solvate.

The present invention also encompasses a crystalline form of Vemurafenib, designated Form T-1. Form T-1 can be characterized by one or more of the following: a powder XRD pattern having peaks at 7.6, 9.9, 13.0, 15.9 and 20.5 degrees 2-theta±0.2 degrees 2-theta; a powder XRD pattern substantially as shown in FIG. 1; and any combinations of these data.

Alternatively, Form T-1 can be characterized by a powder XRD pattern having peaks at 7.6, 9.9, 13.0, 15.9 and 20.5 degrees 2-theta±0.2 degrees 2-theta and also having any one, two, three, four, five or six peaks selected from 8.4, 11.6, 18.8, 24.8, 25.3 and 38.7 degrees 2-theta±0.2 degrees 2-theta.

Figure 2:
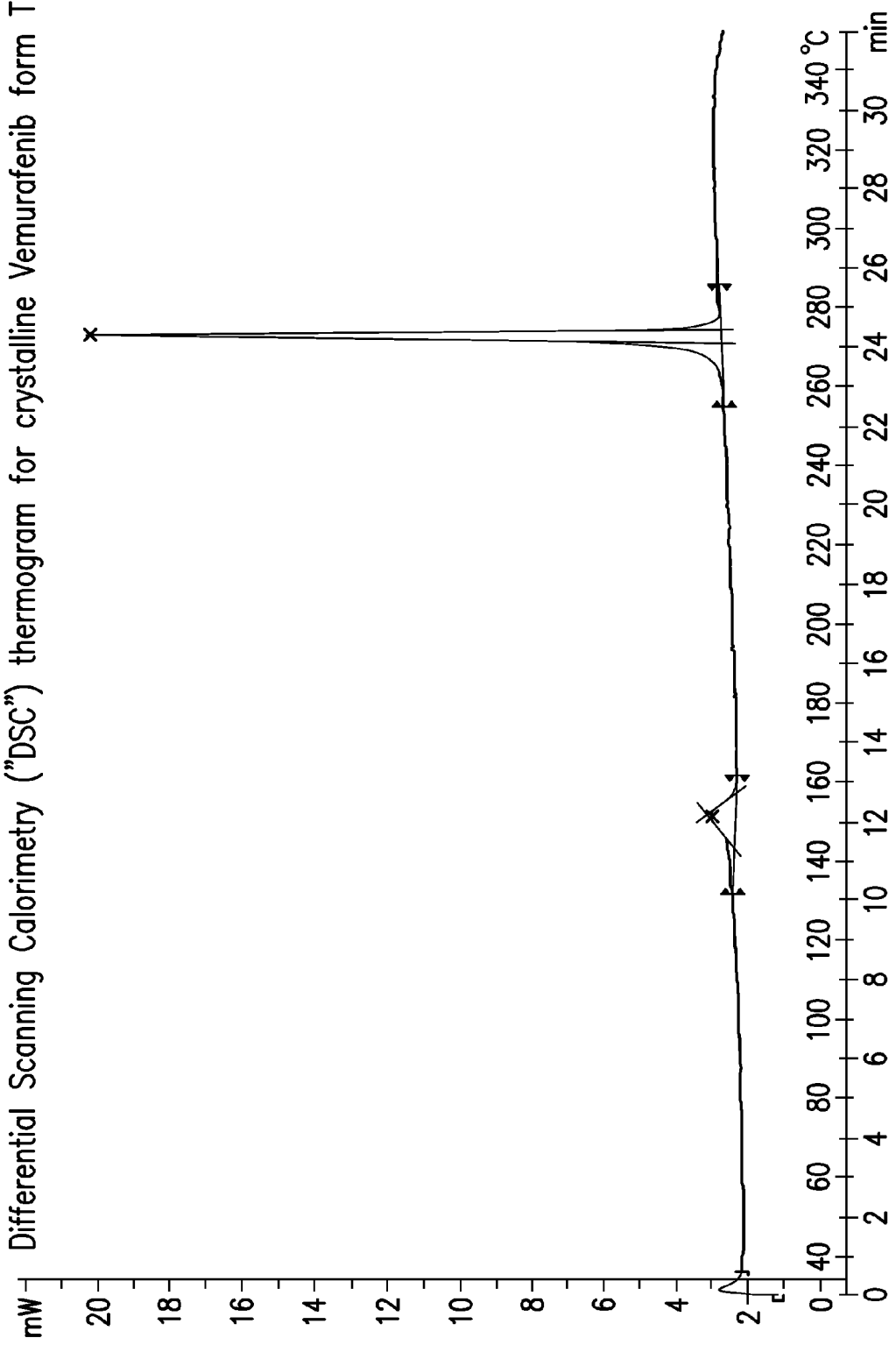
FIG. 2 shows a Differential Scanning Calorimetry ("DSC") thermogram for crystalline Vemurafenib form T-1.

Form T-1 can be further characterized by a DSC thermogram substantially as shown in FIG. 2.

Figure 3:
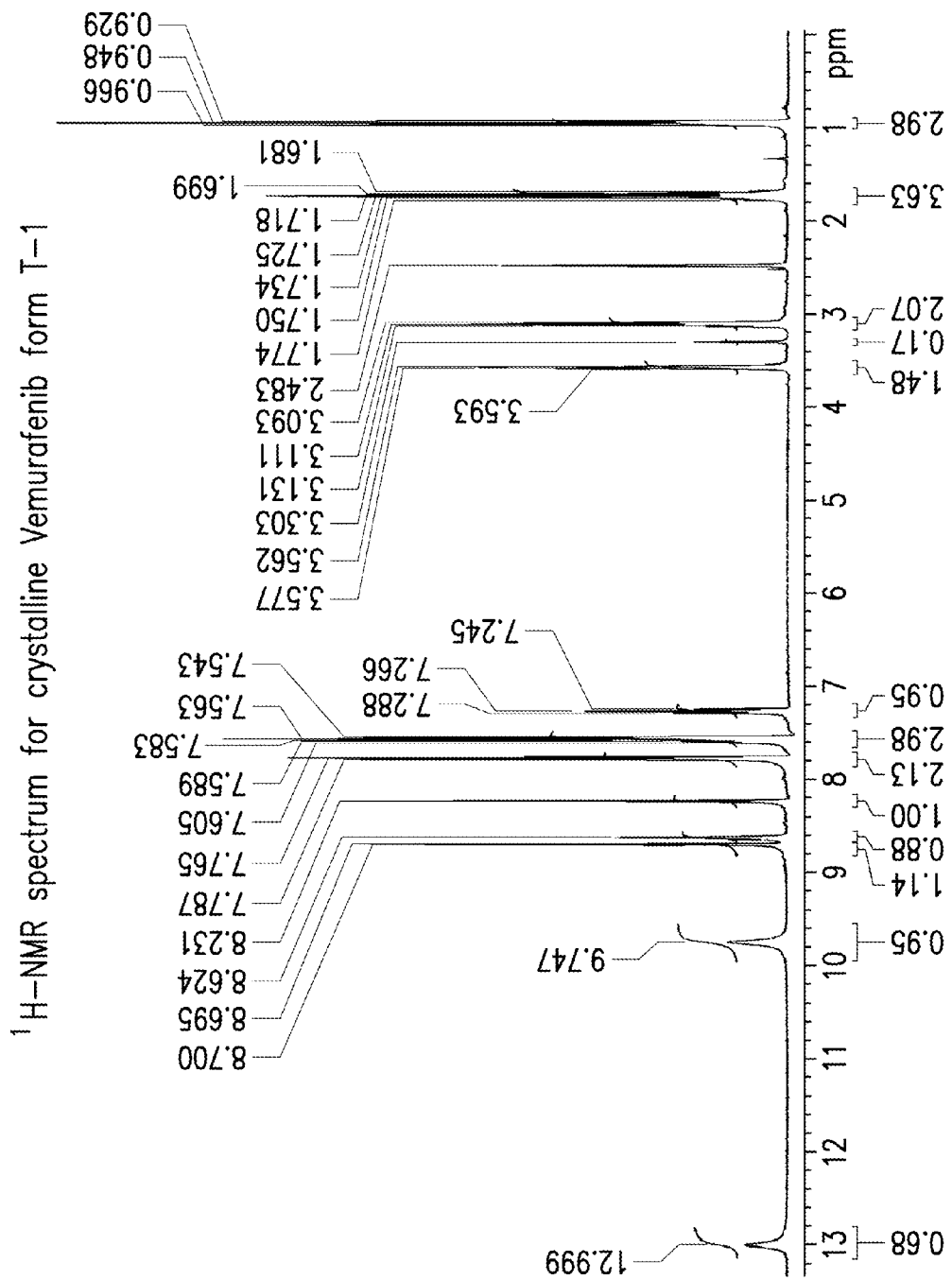
FIG. 3 shows $^1$H-NMR spectrum for crystalline Vemurafenib form T-1.

The above form T-1 can be a THF solvate. The T-1 solvate can have a THF content of about 0.25 to about 0.50 mole equivalents of THF per one mole equivalent of Vemurafenib, as measured by $^1$H-NMR. The $^1$H-NMR of form T-1 is shown in FIG. 3.

It will be understood that Form T-1 can be defined by any possible combination of the data listed above.

The above solid state form of Vemurafenib can be used to prepare Vemurafenib salts and solid state forms thereof. The above solid state forms of Vemurafenib can be also used to prepare pharmaceutical compositions and formulations.

The present invention further provides Vemurafenib esylate salt.

Figure 4:
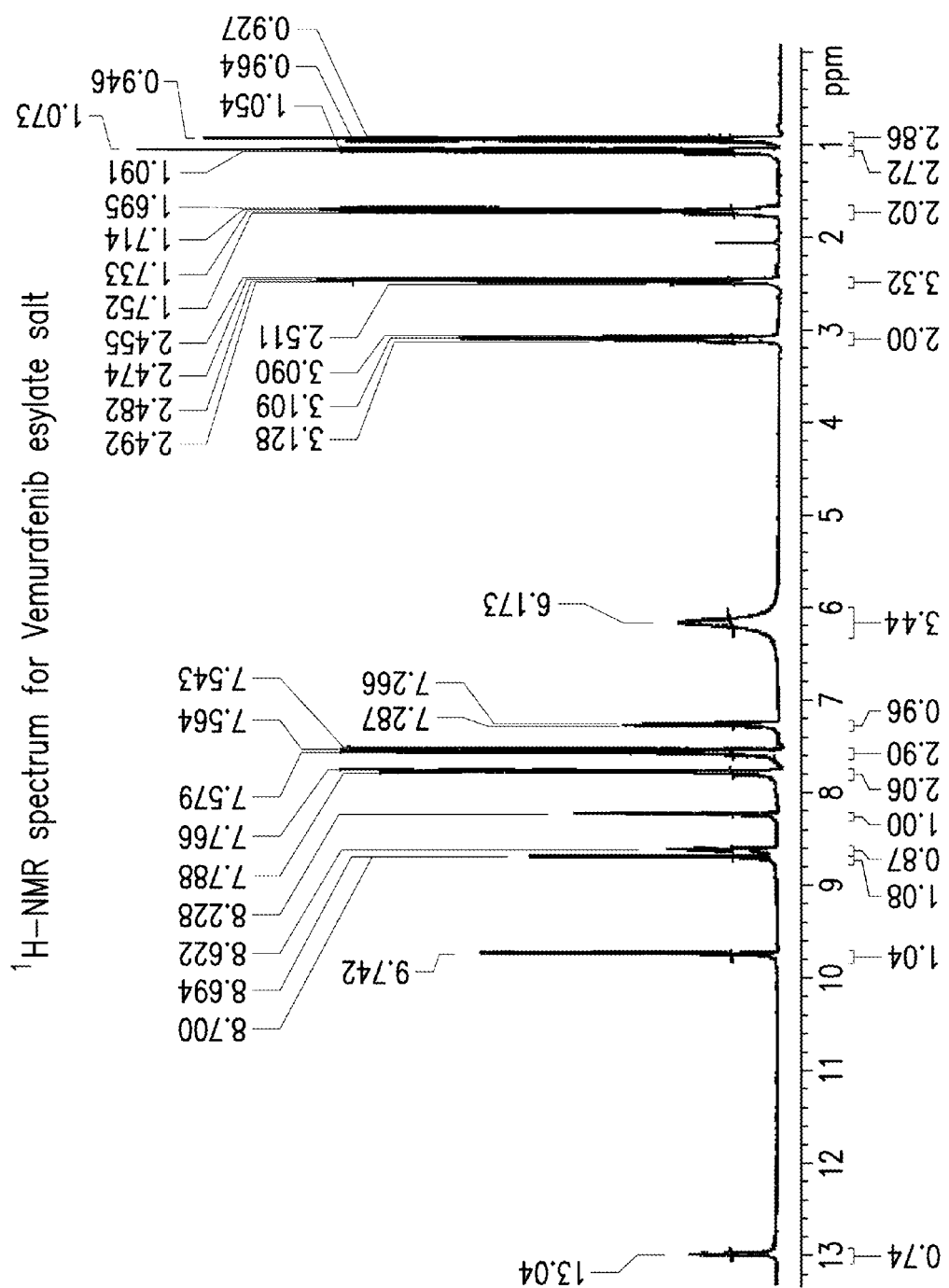
FIG. 4 shows a $^1$H-NMR spectrum for Vemurafenib esylate salt.

The Vemurafenib esylate salt can be characterized by a $^1$H-NMR spectrum substantially as shown in FIG. 4. The Vemurafenib esylate salt can be solid, preferably a crystalline solid.

Figure 5:
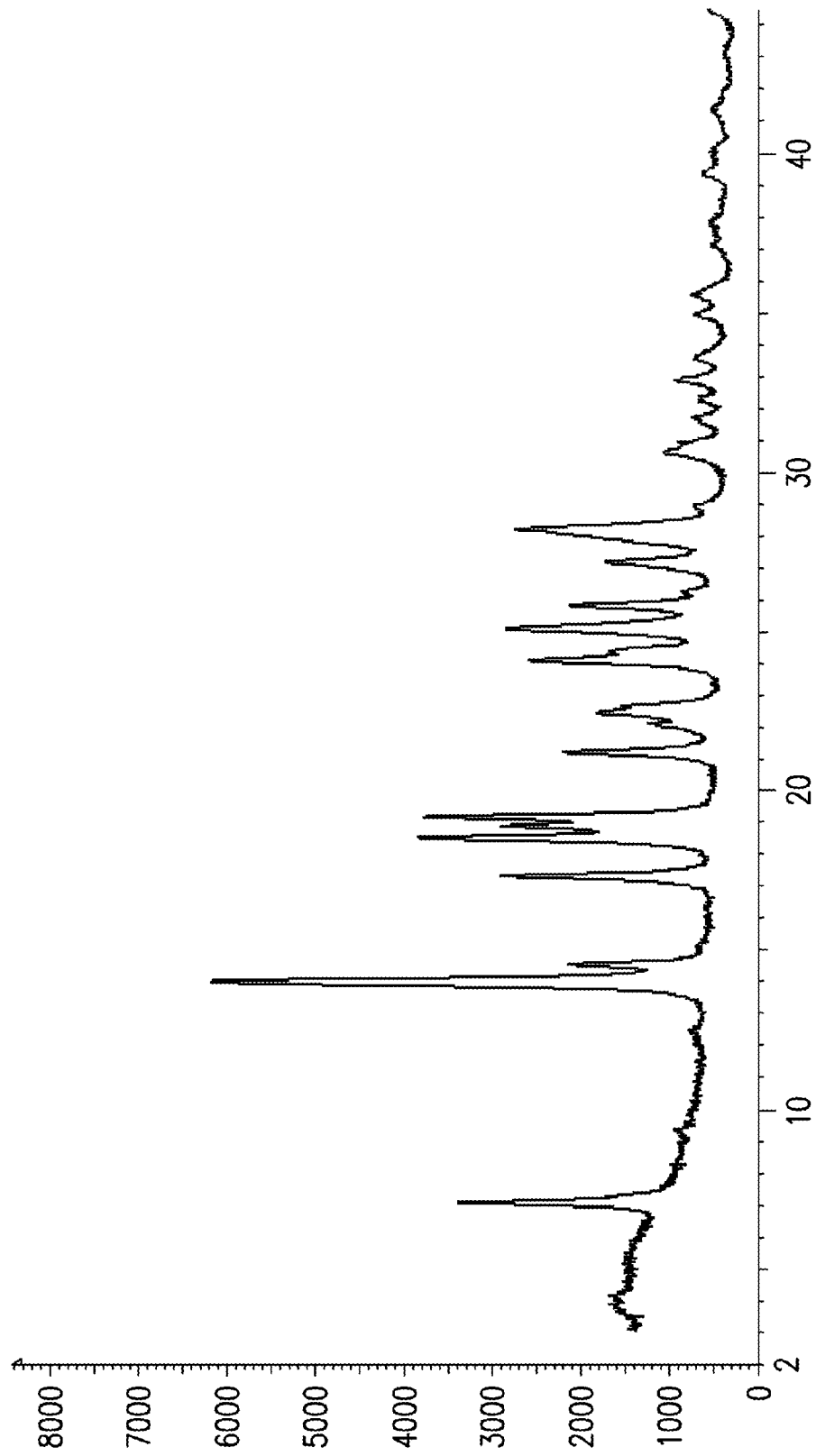
FIG. 5 shows a powder X-ray diffraction pattern for crystalline Vemurafenib esylate form E1.

The present invention also provides a crystalline form of Vemurafenib esylate designated as Form E1. Form E1 can be characterized by one or more of the following: a powder XRD pattern having peaks at 7.0, 13.9, 17.3, 18.5, 18.8 and 19.1 degrees 2-theta±0.2 degrees 2-theta; a powder XRD pattern substantially as shown in FIG. 5; and any combinations of these data.

Alternatively, Form E1 can be characterized by a powder XRD pattern having peaks at 7.0, 13.9, 17.3, 18.5, 18.8 and 19.1 degrees 2-theta±0.2 degrees 2-theta and also having any one, two, three, four or five peaks selected from 14.5, 21.1, 22.4, 25.8 and 27.1 degrees 2-theta±0.2 degrees 2-theta.

Figure 6:
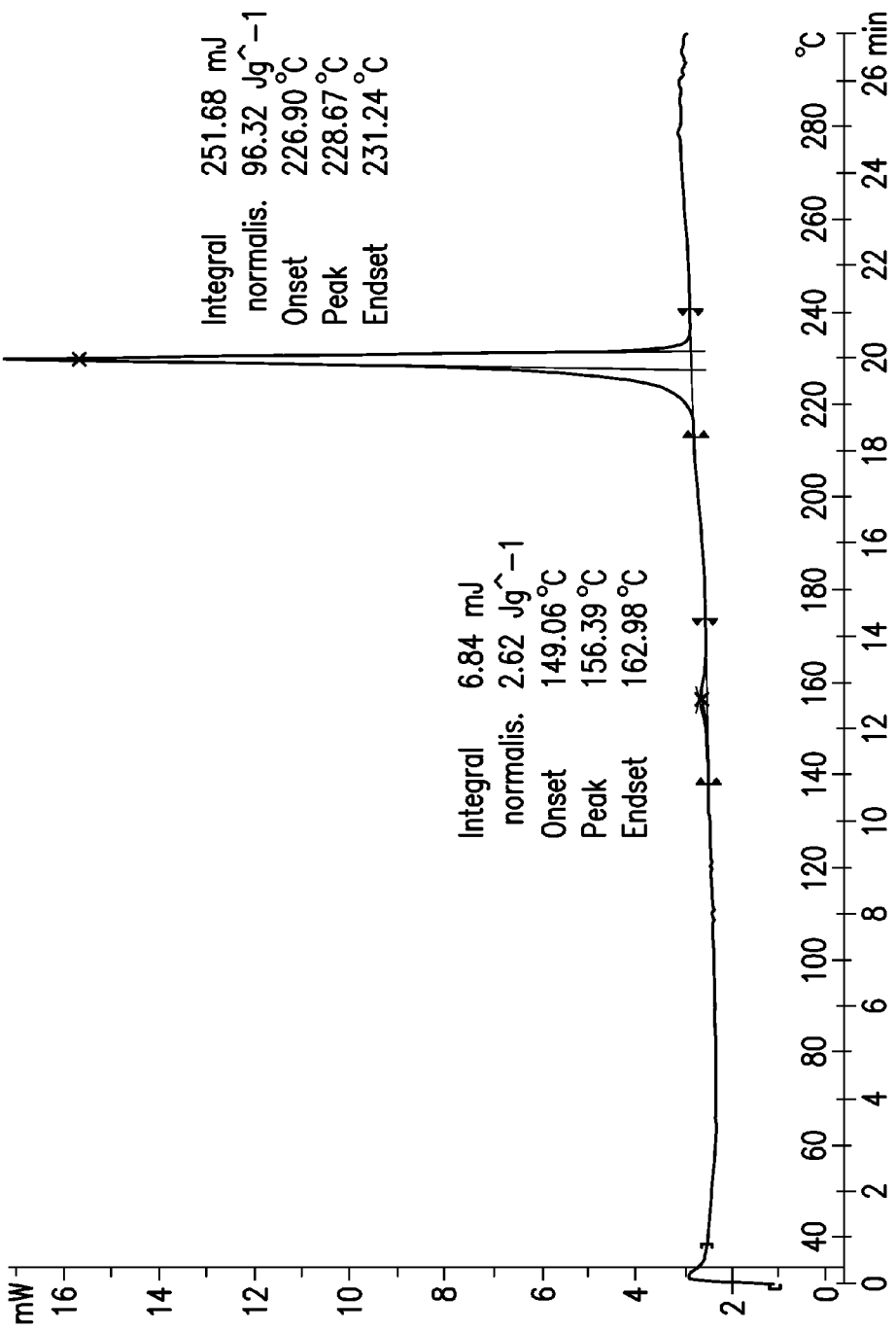
FIG. 6 shows a Differential Scanning Calorimetry ("DSC") thermogram for crystalline Vemurafenib esylate form E1.

Form E1 can be further characterized by a DSC thermogram substantially as shown in FIG. 6.

The above form E1 can be an anhydrous form.

It will be understood that Form T-1 can be defined by any possible combination of the data listed above.

The present invention also provides Vemurafenib choline salt.

Figure 7:
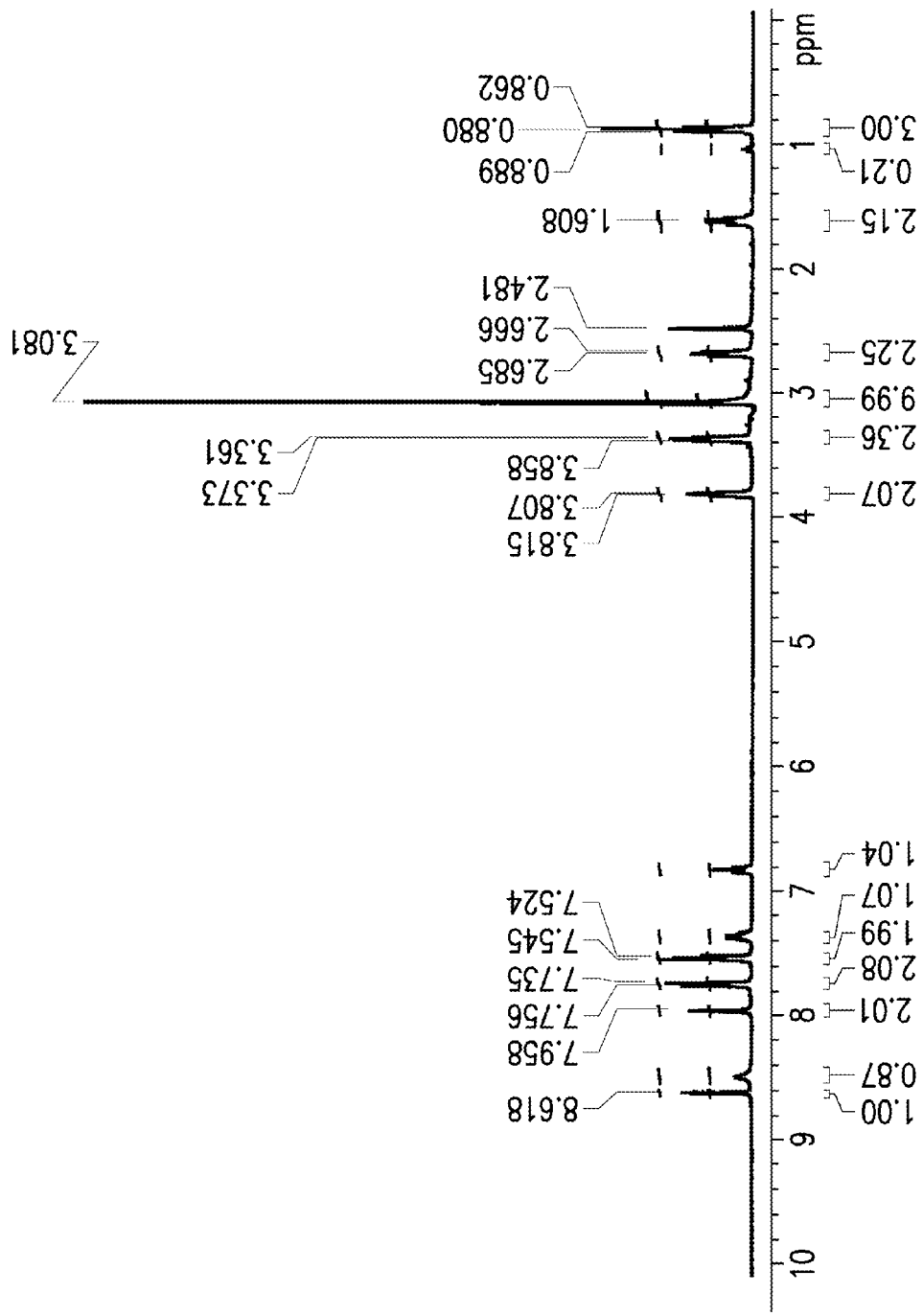
FIG. 7 shows a $^1$H-NMR spectrum for Vemurafenib choline salt.

The Vemurafenib choline salt can be characterized by a $^1$H-NMR spectrum substantially as shown in FIG. 7. The Vemurafenib choline salt can be solid, preferably a crystalline solid.

Figure 8:
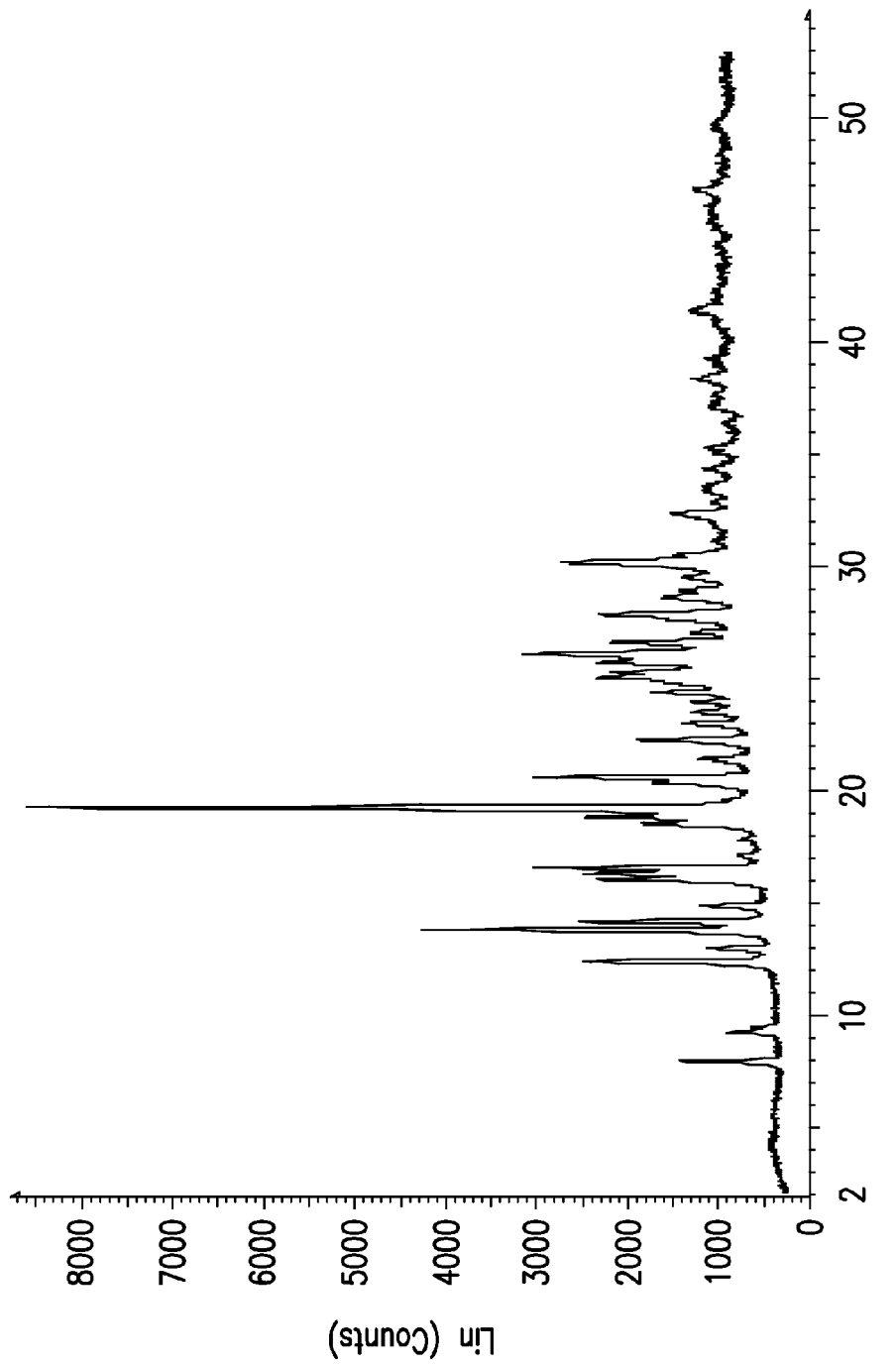
FIG. 8 shows a powder X-ray diffraction pattern for crystalline Vemurafenib choline form C1.
Figure 16:
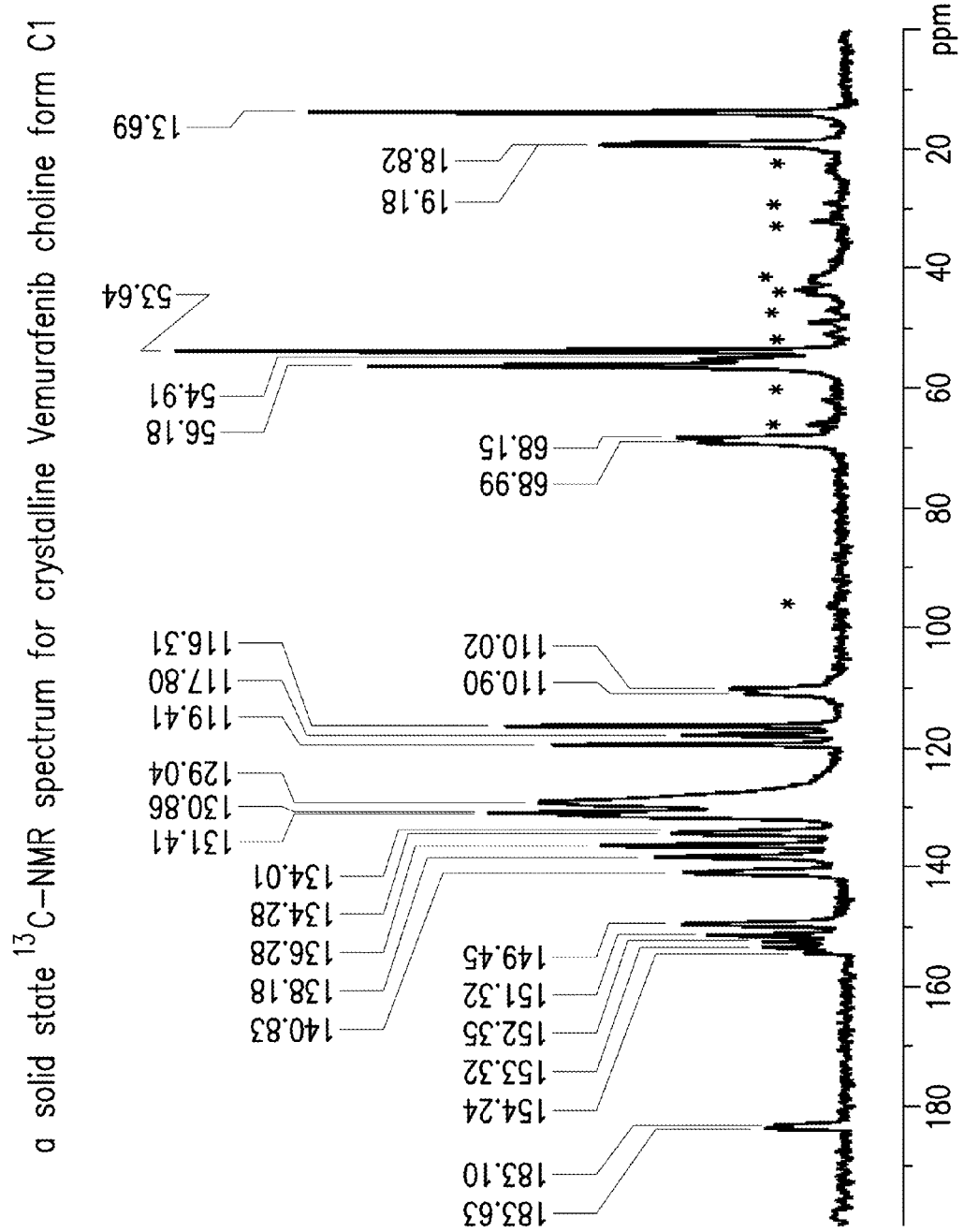
FIG. 16 shows a solid state $^{13}$C NMR spectrum for crystalline Vemurafenib choline form C1.

The present invention also provides a crystalline form of Vemurafenib choline designated Form C1. Form C1 can be characterized by one or more of the following: a powder XRD pattern having peaks at 7.9, 12.4, 13.8, 19.2 and 20.6 degrees 2-theta±0.2 degrees 2-theta; a powder XRD pattern substantially as shown in FIG. 8; a solid-state 13C NMR spectrum having characteristic peaks at 136.3, 119.4, 116.3, 56.2 and 53.6 ppm, ±0.2 ppm; a solid state 13C NMR spectrum having chemical shift differences between said characteristic peaks and a peak at 149.5 ppm±0.2 ppm of −13.2, −30.1, −33.2, −93.3 and −95.9 ppm±0.1 ppm, respectively; a solid state $^{13}$C NMR spectrum substantially as shown in FIG. 16; and combinations of these data.

Typically, the signal exhibiting the lowest chemical shift in the chemical shift area of 0 to 200 ppm is at 13.7±1 ppm.

Alternatively, Form C1 can be characterized by a powder XRD pattern having peaks at 7.9, 12.4, 13.8, 19.2 and 20.6 degrees 2-theta±0.2 degrees 2-theta and also having any one, two, three, four or five peaks selected from 13.0, 14.1, 16.0, 16.3 and 16.6 degrees 2-theta±0.2 degrees 2-theta.

Figure 9:
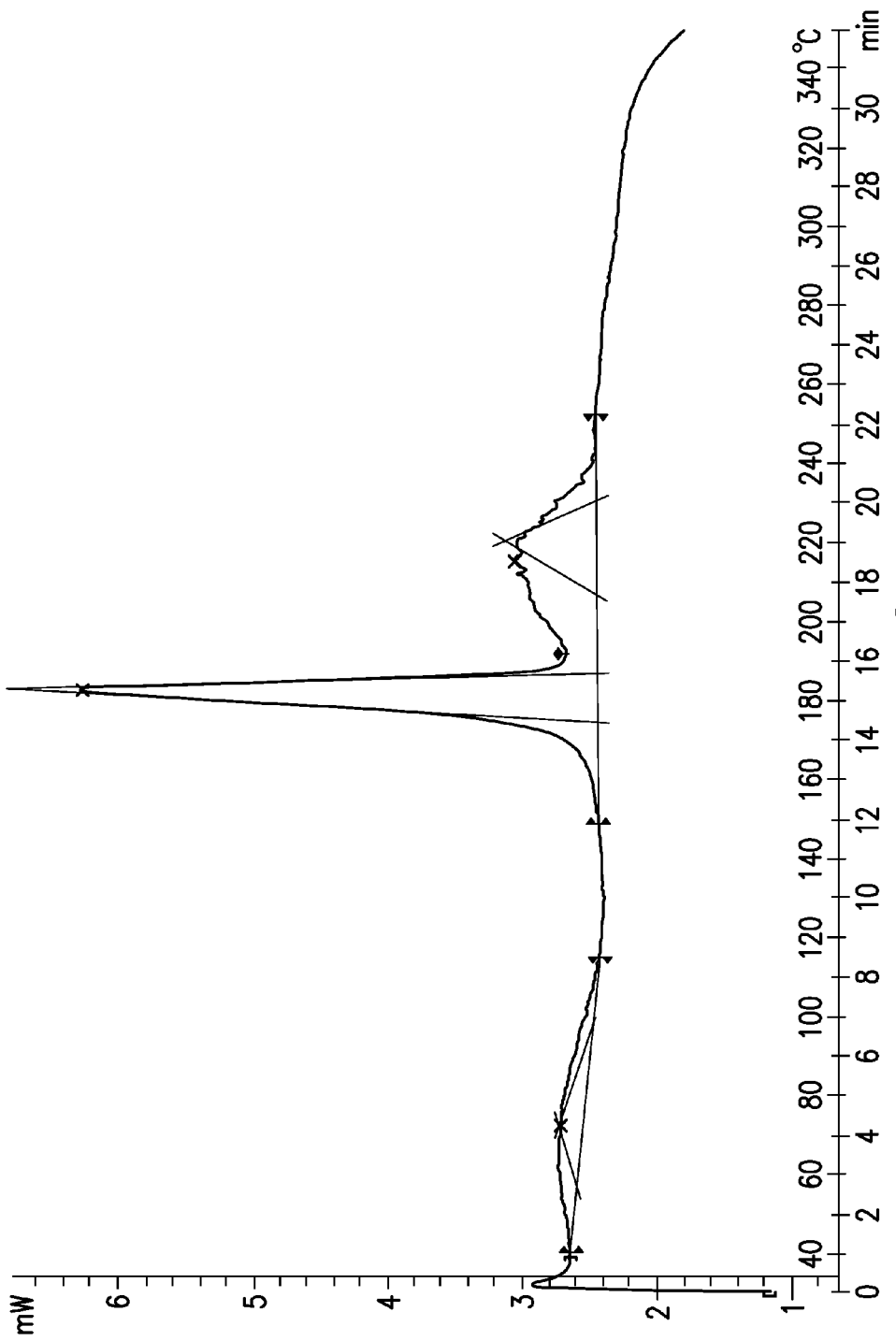
FIG. 9 shows a Differential Scanning Calorimetry ("DSC") thermogram for crystalline Vemurafenib choline form C1.

Form C1 can be further characterized a DSC thermogram substantially as shown in FIG. 9.

Form C1 can be an anhydrous form.

Crystalline Form C1 of Vemurafenib choline may be characterized by each of the above characteristics alone and/or by all possible combinations, e.g. by an X-ray powder diffraction pattern having peaks at 7.9, 12.4, 13.8, 19.2 and 20.6 degrees two theta±0.2 degrees two theta and an X-ray powder diffraction pattern as depicted in FIG. 8, or a DSC thermogram exhibiting the peaks as depicted in FIG. 9.

Depending on which other solid state form they are compared with, the Vemurafenib and Vemurafenib salts and crystalline forms may have advantageous properties selected from at least one of: chemical or polymorphic purity, flowability, solubility, dissolution rate, bioavailability, morphology or crystal habit, stability—such as such as chemical stability as well as thermal and mechanical stability with respect to polymorphic conversion, storage stability, stability to dehydration, low hygroscopicity, and low content of residual solvents and advantageous processing and handling characteristics such as compressibility, or bulk density.

Particularly, the Vemurafenib choline salt, especially crystalline Form C1, is non-hygroscopic and has high chemical purity. Moreover, it exhibits good aqueous solubility properties, e.g. an improved aqueous solubility compared to Vemurafenib. Additionally, crystalline Form C1 is stable upon storage at ambient conditions (i.e. room temperature and atmospheric humidity) for a period of at least 7 months and it is also stable at 45° C. and 75% relative humidity (RH) for at least 2 weeks. Furthermore, Vemurafenib choline, such as the crystalline Form C1 salt, can be used to prepare an oral formulation, i.e. a tablet or a capsule, having relatively small tablet or capsule size as the molar ratio of Vemurafenib to choline, is about 1:1 which is highly advantageous for preparing pharmaceutical compositions with high drug load. Alternative methods of increasing solubility, e.g., a co-precipitate of vemurafenib and a polymer may result in higher ratio of polymer to API, which increases the tablet or capsule size.

The above salts and solid state forms of Vemurafenib can be used to prepare Vemurafenib or other Vemurafenib salts; solid state forms thereof; as well as pharmaceutical compositions and pharmaceutical formulations thereof. It was found that the above salts of Vemurafenib and their solid state forms are, amongst other things, very useful for preparing Vemurafenib with a high degree of purity.

The present invention provides a process for preparing Vemurafenib, for example, by preparing any one of the salts and solid state forms of the present invention; and basifying or acidifying the said salt to obtain Vemurafenib. The process can further comprise converting the obtained Vemurafenib to any other salt of Vemurafenib, or to solid state forms thereof. The conversion can comprise, for example, reacting the obtained Vemurafenib with an appropriate acid or a base to obtain the corresponding acid addition or base addition salt. Alternatively, the conversion can be done by salt switching, i.e., reacting a Vemurafenib acid addition salt, with an acid having a $pK_a$ which is lower than the $pK_a$ of the acid of the first vemurafenib acid addition salt or reacting a vemurafenib base addition salt, with a base having a $pK_a$ which is higher than the $pK_a$ of the base of the first vemurafenib base addition salt.

The above described solid state forms of Vemurafenib and the Vemurafenib salts and solid state forms thereof can be used to prepare pharmaceutical compositions and pharmaceutical formulations. The present invention provides a process for preparing formulations of Vemurafenib and Vemurafenib salts comprising combining any one or a mixture of the salts and solid state forms of the present invention and at least one pharmaceutically acceptable excipient. The present invention further encompasses 1) pharmaceutical compositions and formulations comprising any one or a combination of the solid state forms of Vemurafenib; Vemurafenib salts or their solid state forms, as described above, and, in the case of pharmaceutical formulations, at least one pharmaceutically acceptable excipient; 2) the use of any one or a combination of the above-described solid state forms of Vemurafenib; Vemurafenib salts or their solid state forms, in the manufacture of a pharmaceutical composition; 3) a method of treating cancer; and 4) one or a combination of solid state forms of Vemurafenib, of Vemurafenib salts, or their solid state forms as described above, for use as a medicament, particularly for treating cancer. The pharmaceutical composition can also be used for preparing a medicament. The present invention also provides crystalline forms as described above for use as a medicament.

The present invention further describes the compound, 2,6-Difluoro-3-[methyl-(propane-1-sulfonyl)-amino]-benzoic acid, referred to herein as Compound 1:

Compound 1

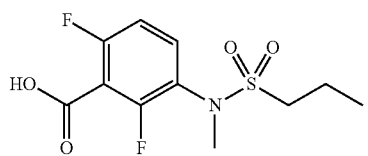

Compound 1 can be an impurity of the Vemurafenib intermediate, 2,6-Difluoro-3-(propane-1-sulfonylamino)-benzoic acid, referred to herein as Compound 1a:

Compound 1a

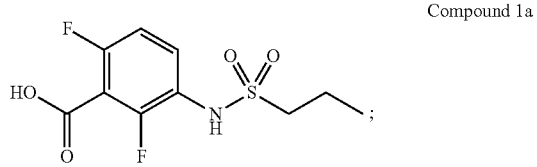 [SMILES: CCCS(=O)(=O)Nc1ccc(F)c(C(=O)O)c1F]

and can further react as the synthesis proceeds and thus contaminate the final Vemurafenib product.

The present invention also describes the compound, Propane-1-sulfonic acid {3-[5-(4-chloro-phenyl)-1H-pyrrolo[2,3-b]pyridine-3-carbonyl]-2,4-difluoro-phenyl}-methylamide, referred to herein as N-methyl Vemurafenib or Compound 2:

Compound 2

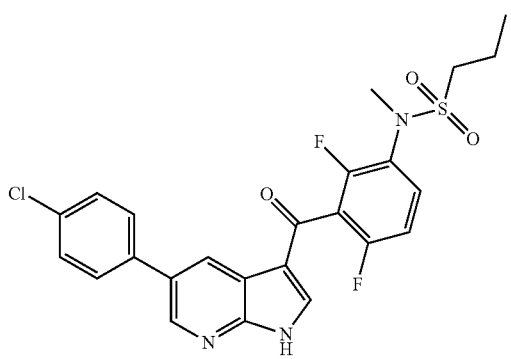

Figure 10:
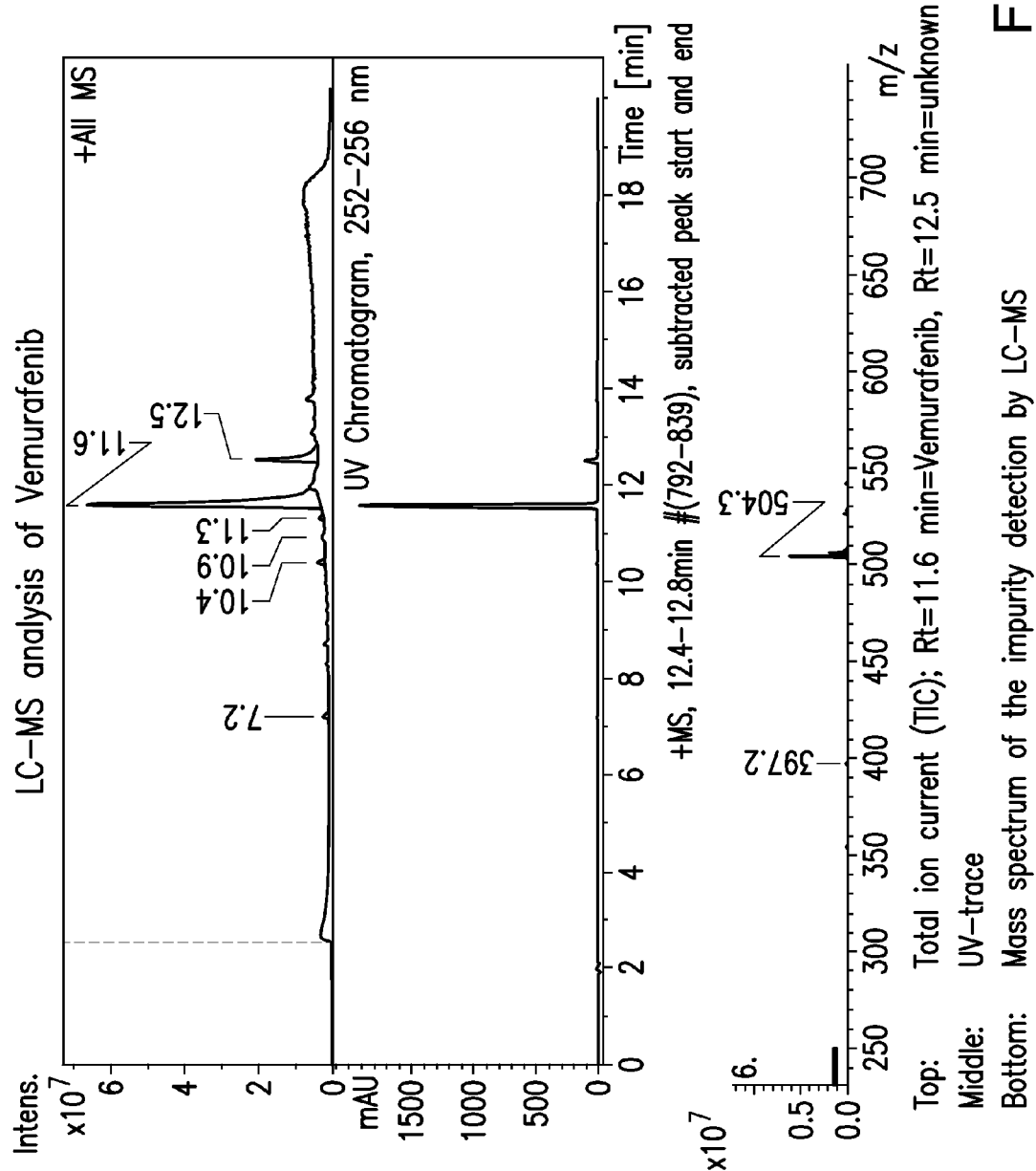
FIG. 10 shows a LC-MS analysis of Vemurafenib.

Compound 2 has a molecular weight of 503 ([M+H]$^+$=m/z 504) (determined by LC-MS analysis, presented in FIG. 10).

Compound 2 can be characterized by suitable analytical methods, such as a $^1$H-NMR, $^{13}$C-NMR and IR.

Figure 11:
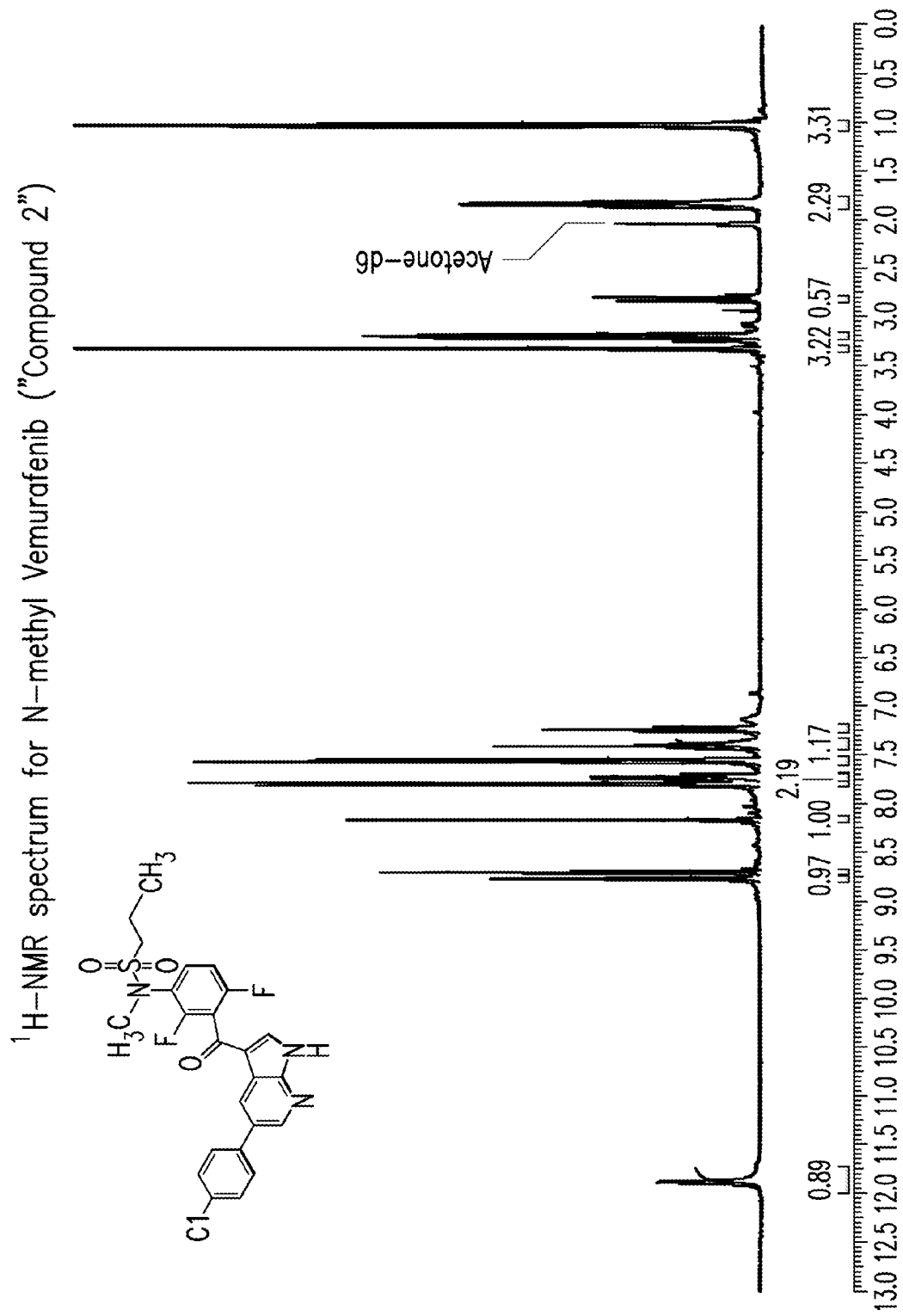
FIG. 11 shows a $^1$H-NMR spectrum for N-methyl Vemurafenib ("Compound 2").

$^1$H NMR (400 MHz, ACETONE-d$_6$) δ ppm 1.03 (t, J=7.43 Hz) 1.84 (m, 2H) 3.20 (m, 2H) 3.32 (s, 3H) 7.23 (m, 1H) 7.40 (m, J=6.26, 6.26 Hz) 7.55 (d, J=8.60 Hz, 2H) 7.72 (m, 1H) 7.79 (d, J=8.60 Hz, 2H) 8.16 (s, 1H) 8.70 (d, J=2.35 Hz, 1H) 8.76 (s, 1H) 11.88 (s, 1H). A $^1$H NMR spectrum of compound 2 is shown in FIG. 11.

Figure 12:
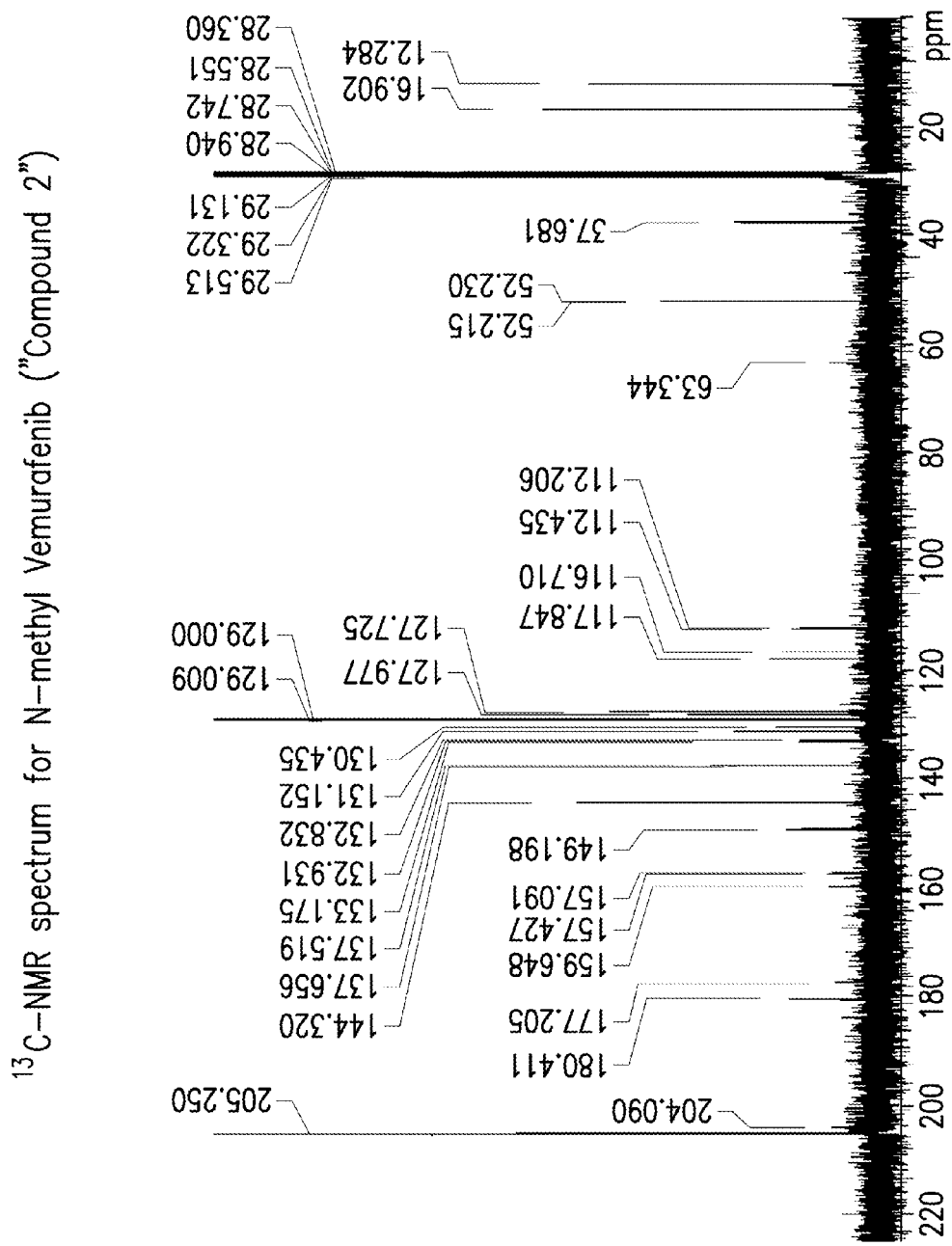
FIG. 12 shows a $^{13}$C-NMR spectrum for N-methyl Vemurafenib ("Compound 2").

$^{13}$C NMR (100 MHz, ACETONE-d$_6$) δ ppm 12.3, 16.9, 37.7, 52.2, 63.3, 112.2, 112.4, 116.7, 117.8, 127.7, 128.0, 129.0, 129.1, 130.4, 131.1, 132.8, 132.9, 133.2, 137.5, 137.7, 144.3, 149.2, 157.1, 157.4, 159.6, 177.2, 180.4, 204.1. A $^{13}$C NMR spectrum of compound 2 is shown in FIG. 12.

Figure 13:
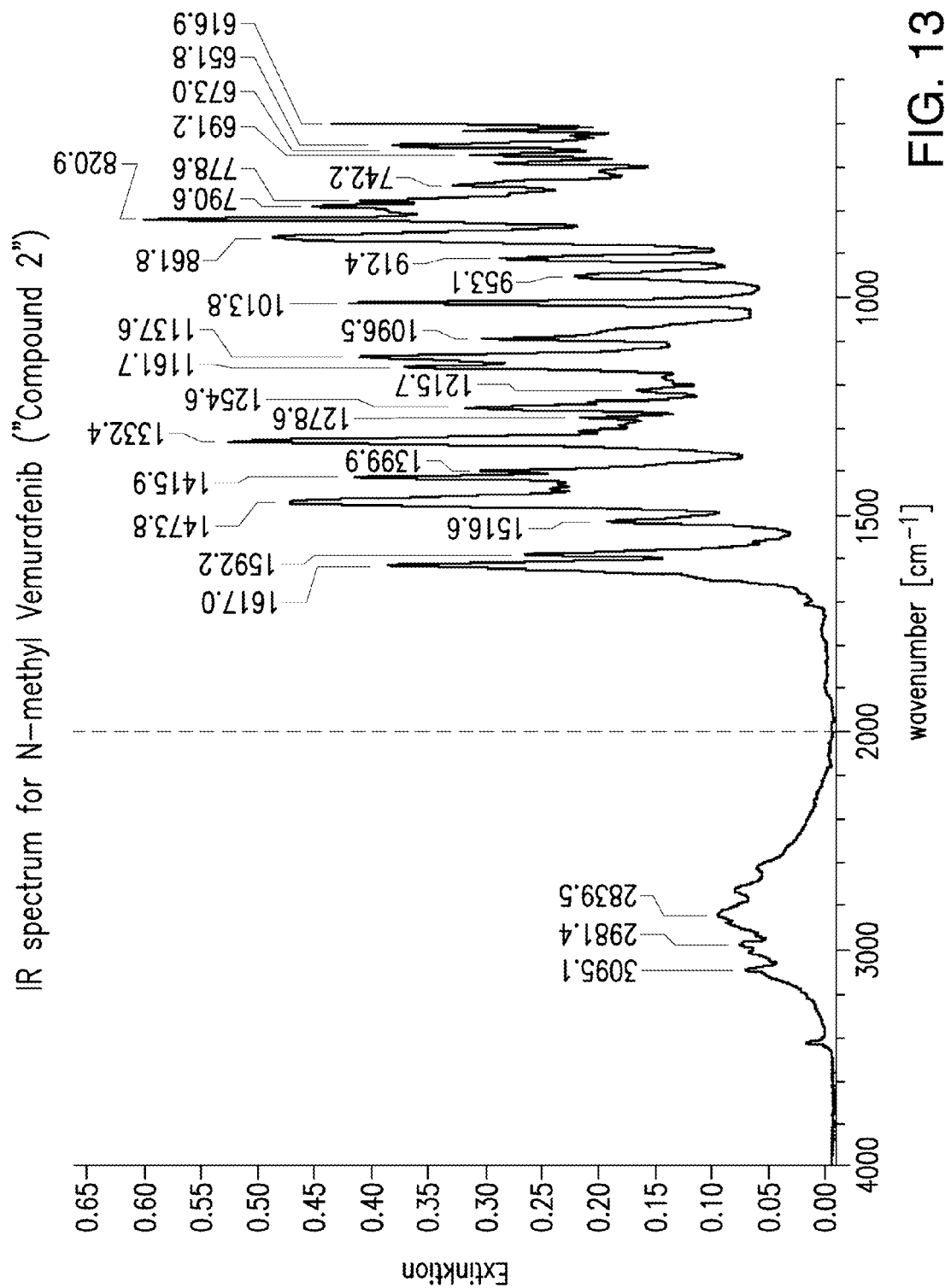
FIG. 13 shows an IR spectrum for N-methyl Vemurafenib ("Compound 2").
Figure 14:
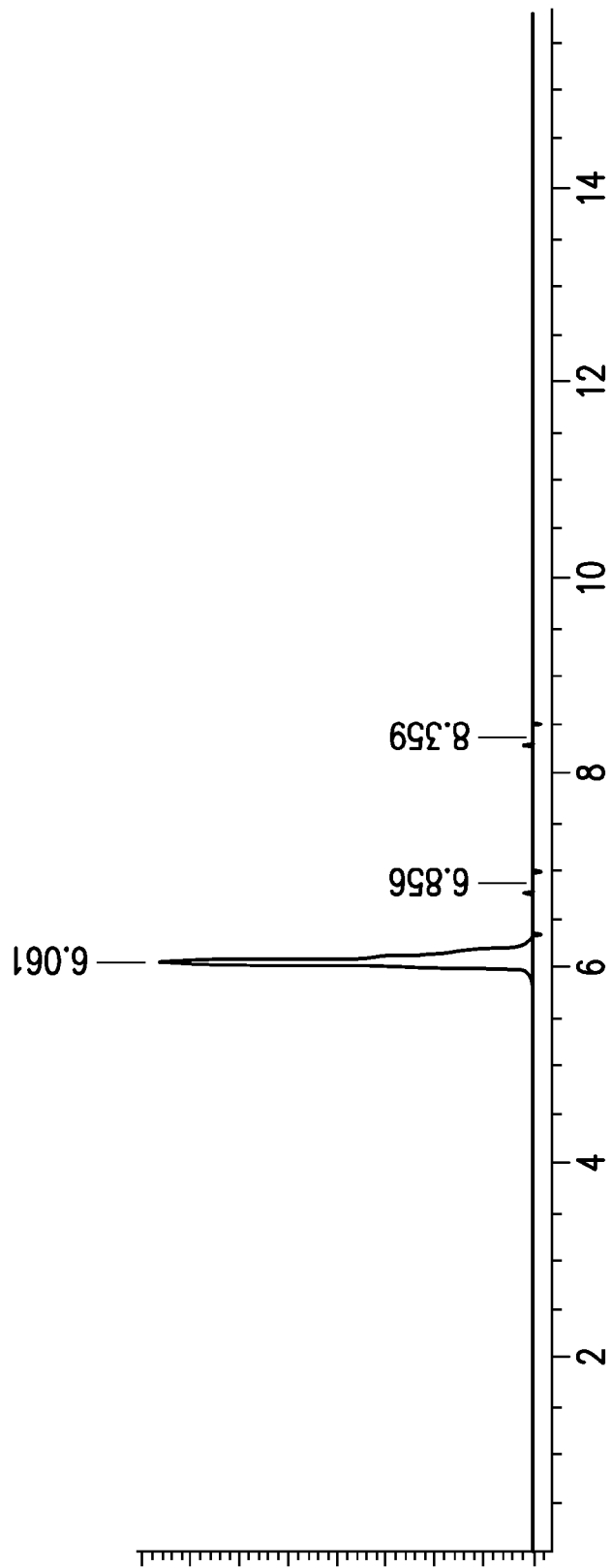
FIG. 14 shows an HPLC chromatogram of Vemurafenib.
Figure 15:
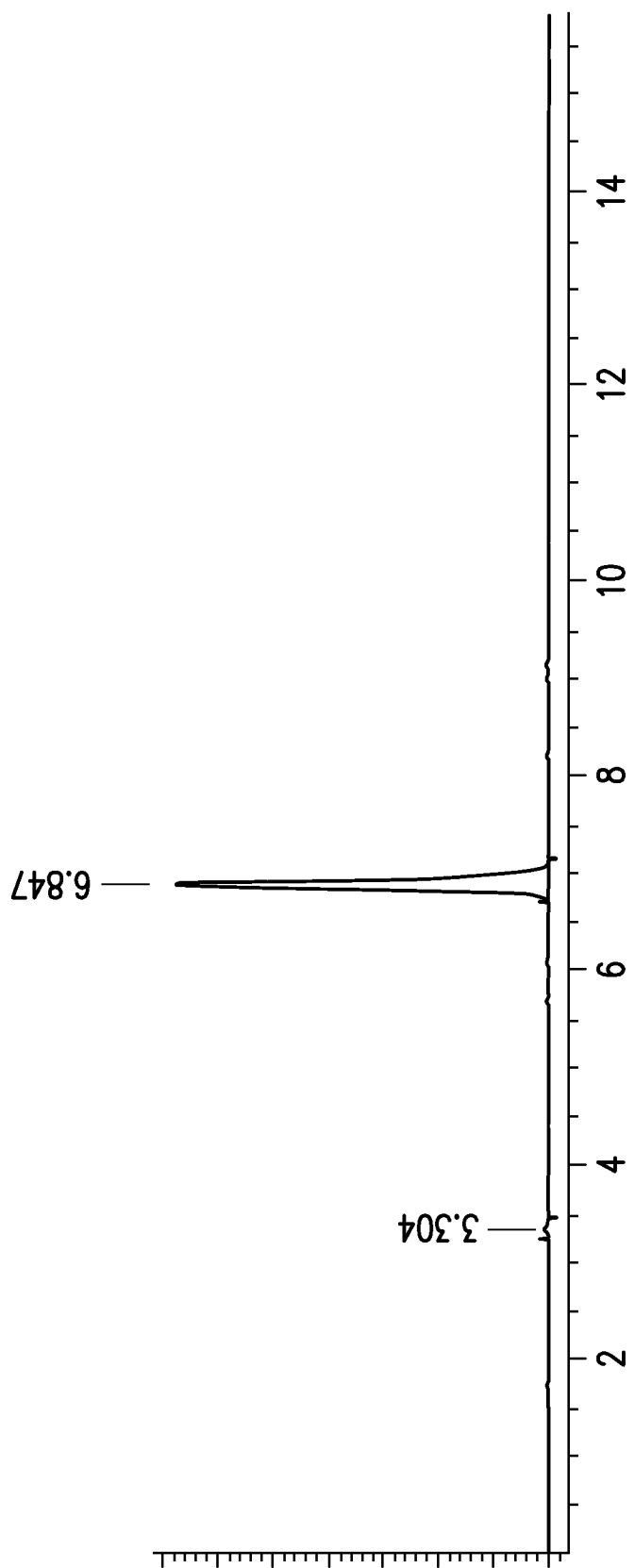
FIG. 15 shows an HPLC chromatogram of N-methyl Vemurafenib ("Compound 2").

IR (ATR) [cm$^{-1}$]: 3095, 2981, 2840, 1617, 1592, 1474, 1416, 1332, 1255, 1162, 1138, 1097, 1014, 953, 912, 862, 821, 791, 652. An IR spectrum of compound 2 is shown in FIG. 13.

Compound 2 can be characterized by any combination of the above described data.

The above Compound 1 and Compound 2 can for example be used as reference markers and as reference standards to analyze the purity of Vemurafenib and to quantify the amount of those impurities in a sample of Vemurafenib. In a further embodiment, the invention is directed to analytical methods for testing or determining the impurity profile of Vemurafenib by using the above-described Compounds 1 and/or 2.

Having described the invention with reference to certain preferred embodiments, other embodiments will become apparent to one skilled in the art from consideration of the specification. The invention is further illustrated by reference to the following examples describing in detail the preparation of the composition and methods of use of the invention. It will be apparent to those skilled in the art that many modifications, both to materials and methods, may be practiced without departing from the scope of the invention.

Nuclear Magnetic Resonance (NMR) Spectroscopy Method:
Instrument: Varian Mercury 400 Plus NMR Spectrometer, Oxford AS, 400 MHz.
The samples were dissolved in DMSO-d6.

Powder X-Ray Diffraction Pattern ("PXRD") Method:
The sample was analyzed on a D8 Advance X-ray powder diffractometer (Bruker-AXS, Karlsruhe, Germany). The samples were layered onto a silicon specimen holder. The sample holder was rotated in a plane parallel to its surface at 20 rpm during the measurement. Further conditions for the measurements are summarized below. The raw data were analyzed with the program EVA (Bruker-AXS, Germany).

| | Standard measurement |
|---|---|
| radiation | Cu K$_\alpha$ (λ = 1.5418 Å) |
| source | 38 kV/40 mA |
| detector | Vantec |
| detector slit | Variable |
| divergence slit | v6 |
| antiscattering slit | v6 |
| 2θ range/° | 2 ≤ 2θ ≤ 55 |
| step size/° | 0.017 |

Differential Scanning Calorimetry ("DSC") Method:
Crystalline Vemurafenib Form T-1:
Instrument: Mettler Toledo DSC 822E coupled with a Mettler Toledo Gas-Flow-Controller TS0800GC1 (Mettler-Toledo GmbH, Gießen, Germany)
Aluminium crucible: 40 μL
Lid: perforated
Temperature range: 30° C. to 350° C.

Heating rate: 10° C./min
Nitrogen flush: 50 mL/min
Software: STARe Version. 8.10
Interpretation: Endothermic modus
Crystalline Vemurafenib Esylate Form E1 and Crystalline Vemurafenib Choline Form C1:
Instrument: Varian Mercury 400 Plus NMR Spectrometer, Oxford AS, 400 MHz
Instrument: Mettler Toledo DSC 822E coupled with a Mettler Toledo Gas-Flow-Controller TS0800GC1 (Mettler-Toledo GmbH, Gießen, Germany)
Aluminium crucible: 40 µL
Lid: Perforated
Temperature range: 30° C. to 300° C.
Heating rate: 10° C./min
Nitrogen flush: 50 mL/min
Software: STARe Version. 8.10
Interpretation: Endothermic modus
HPLC/UV Method:
Method A:
Instrument: Agilent 1200
Injection volume: 2 µl
Solvent A: acetonitrile
Solvent B: 0.2% formic acid +0.1% HFBA pH.2.21
Flow: 0.7 ml/min
Temperature: 40° C.
Column: Phenomenex Kinetex C18 100A, 150*4.6 mm, 2.6 µm

| time [min] | solvent B [%] |
|---|---|
| 0.00 | 40 |
| 8.00 | 15 |
| 20.00 | 15 |
| 20.00 | 40 |

LC-MS method:
Instrument: Agilent 1200 coupled with Esquire HCT (Bruker Daltonics)
Chromatographic conditions:
Instrument: Agilent 1200
Injection volume: 2 µm
Solvent A: acetonitrile
Solvent B: 0.2% formic acid +0.1% HFBA pH.2.21
Flow: 0.7 ml/min
Temperature: 40° C.
Column: Phenomenex Kinetex C18 100A, 150*4.6 mm, 2.6 µm

TABLE 1

| time [min] | solvent B [%] |
|---|---|
| 0.00 | 40 |
| 8.00 | 15 |
| 20.00 | 15 |
| 20.00 | 40 |

Hygroscopicity Method

Vapour sorption experiments were performed in the instrument SPSx-1µ (Projekt Messtechnik, Ulm, Germany) at a temperature of 25° C. with the humidity cycles as shown below.

TABLE 2

Humidity cycle conditions.

| Cycle No. | Humidity conditions (% RH) start value | end value | Number of steps | Time (h) |
|---|---|---|---|---|
| 1 | 40 | 0 | 4 | — |
| 2 | 5 | 95 | 9 | — |
| 3 | 90 | 0 | 9 | — |
| 4 | 5 | 35 | 3 | — |

Aqueous Saturation Solubility

Solubility of Vemurafenib choline Form C1 was determined at RT using a magnetic stirrer for parallel synthesis at 150 rpm. About 3 mg of the salt were suspended in phosphate buffer pH 6.8 (USP)+1% hexadecyltrimethylammonium bromide (HTAB). The sample was stirred for 15 sec, filtrated through a PTFE filter 0.2µ and analyzed via HPLC. The results for aqueous saturation solubility are shown in Table 3.

TABLE 3

Aqueous saturation solubility of Vemurafenib choline.

| Salt | Batch no. | Phosphate buffer pH 6.8 + 1% HTAB | | Phosphate buffer pH 6.5 + 2% TPGS, 5 min Reax | |
|---|---|---|---|---|---|
| | | Solubility (mg/mL) | Classification (USP) | Solubility (mg/mL) | Classification (USP) |
| Vemurafenib | FL890 | 0.007 | — | 0.013 | — |
| Vemurafenib Choline crystalline C1 | FL940 | 0.752 | — | 1.292 | — |

EXAMPLES

The starting Vemurafenib (also referred to as Vemurafenib free base) can for example be prepared by the process disclosed in U.S. Pat. No. 7,863,288, example 3, which is incorporated by reference in its entirety.

Example 1

Preparation of Crystalline Vemurafenib Form T-1

Vemurafenib free-base (200 mg) was dissolved in 5 mL tetrahydrofuran at room temperature. Distilled water (10 ml) was added dropwise while stirring (500 rpm) at room temperature. Stirring was continued for 2 h and the obtained suspension was left for an additional 22 h at room temperature. The resulting precipitate was isolated by filtration and dried under reduced pressure (20 mbar) at 40° C. to yield the Vemurafenib THF solvate as a slightly yellow powder.

Example 2

Preparation of Crystalline Vemurafenib Form T-1

Vemurafenib free-base (200 mg) was dissolved in 5 mL tetrahydrofuran at room temperature. tert-Butyl methyl ether (10 ml) was added dropwise while stirring (500 rpm) at room temperature. Stirring was continued for 2 h and the obtained suspension was left for an additional 22 h at room temperature. The resulting precipitate was isolated by filtration and dried under reduced pressure (20 mbar) at 40° C. to yield the Vemurafenib THF solvate as a slightly yellow powder.

Example 3

Preparation of Crystalline Vemurafenib Form T-1

Vemurafenib free-base (200 mg) was dissolved in 5 mL tetrahydrofuran at room temperature. n-Hexane (10 ml) was added dropwise while stirring (500 rpm) at room temperature. Stirring was continued for 2 h and the obtained suspension was left for an additional 22 h at room temperature. The resulting precipitate was isolated by filtration and dried under reduced pressure (20 mbar) at 40° C. to yield the Vemurafenib THF solvate as a slightly yellow powder.

Example 4

Preparation of Crystalline Vemurafenib Esylate Form E1

Vemurafenib free-base (0.5 g) was suspended in 10 mL acetone at 30-35° C. Ethanesulfonic acid (0.11 g) was added at 30-35° C. and the mixture was cooled to 0-5° C. within 30 minutes. The resulting precipitate was isolated by filtration and washed with acetone (2 mL) The product was dried under reduced pressure (20 mbar) at room temperature to yield 0.57 g of Vemurafenib esylate as a white powder.

Example 5

Preparation of Crystalline Vemurafenib Choline Form C1

Vemurafenib (500 mg, 1.0 mmol) was suspended in 5 mL acetone at 35°. A solution of choline hydroxide in methanol (45%, 270 mg, 1.0 mmol) was added and the resulting mixture was stirred at 35° C. for 5 minutes. Then, the resulting clear solution was cooled to 5° C. over 30 minutes and was stirred in the opened vial overnight at room temperature. An oily residue was obtained and 2 mL ethanol was added. The mixture was sonicated (treated with ultra-sonic energy) until a clear solution was obtained. Two drops of n-hexane were added and the mixture was cooled in a refrigerator for 9 days. The obtained precipitate was filtered, washed with ethanol and dried under normal pressure at room temperature to yield 200 mg (33%) Vemurafenib choline as a white solid. (Purity: 98.4% by HPLC)

Example 6

Preparation of Crystalline Vemurafenib Choline Form C1

To a stirred suspension of Vemurafenib base (1.5 g, 3.1 mmol) and 15 ml acetone (T=30-35° C.), 0.9 ml (3.1 mmol) choline (45% in methanol) was added. The obtained solution was stirred for 5 min at 35° C. then cooled to 5° C., stirred at this temperature for 30 min and then allowed to warm to RT. During overnightstirring in the open vial, the solvent evaporated. To the oily residue, 5 ml ethanol was added. The mixture was placed in an ultrasonic bath until a clear solution was obtained. After the solution was stored in the refrigerator for 3 days, a precipitate was formed which was filtered off, washed with 2 ml ethanol and dried at RT O/N. 0.54 g (yield: 29.7%) Vemurafenib choline salt was isolated in high purity (HPLC/UV: 99.4 area %).
XRPD and DSC analysis confirmed that the solid state corresponded to that of Form C1.

Example 7

Preparation of Crystalline Vemurafenib Choline Form C1

To a stirred suspension of 1.5 g Vemurafenib base and 15 ml acetone (T=30-35° C.), 0.9 ml choline (45% in methanol) was added. The obtained solution was stirred for 5 min at 35° C., then cooled to RT and divided into three identical portions. All three portions were stirred O/N in open vials at RT. To the oily residues, 1.5 ml of solvent was added (vial 1: isopropanol, vial 2: ethyl acetate and vial 3: tert. butylmethylether). After treatment in an ultrasonic bath until a clear solution was obtained, the vials were stored in the refrigerator for 6 days, the precipitates were filtered off, washed with 1.5 ml of the same solvent which was used for precipitation and dried O/N at RT.
XRPD analysis confirmed that the solid state of all three samples corresponded to that of Form C1.

Example 8

Preparation of Crystalline Vemurafenib Choline Form C1

To a stirred suspension of 5 g Vemurafenib base and 50 ml acetone (T=30-35° C.), 3.0 ml choline (45% in methanol) was added. The obtained solution was stirred for 5 min at 35° C. and then cooled to RT. After evaporation of the solvent, a solid was obtained. 15 ml isopropanol was added, the suspension was placed in an ultrasonic bath (suspension, no solution was formed) and then stored in the refrigerator for 1 days. The precipitate was filtered off, washed with 5 ml isopropanol and dried at RT O/N. 2.07 g (yield: 80.5%).
XRPD and DSC analysis confirmed that the solid state corresponded to that of Form C1.

Example 9

Preparation of Propane-1-sulfonic acid{3-[5-(4-chloro-phenyl)-1H-pyrrolo[2,3-b]pyridine-3-carbonyl]-2,4-difluoro-phenyl}-methyl-amide, (N-methyl Vemurafenib, "Compound 2")

Step 1: Propane-1-sulfonic acid{3-[5-(4-chloro-phenyl)1-(2,6-dichloro-benzoyl)-1H-pyrrolo[2,3-b]pyridine-3-carbonyl]-2,4-difluoro-phenyl}-methyl-amide

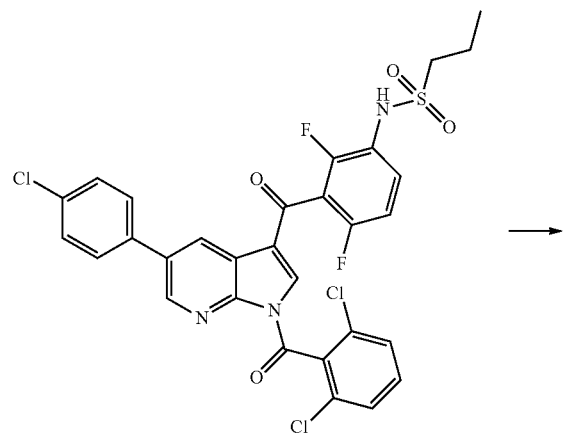

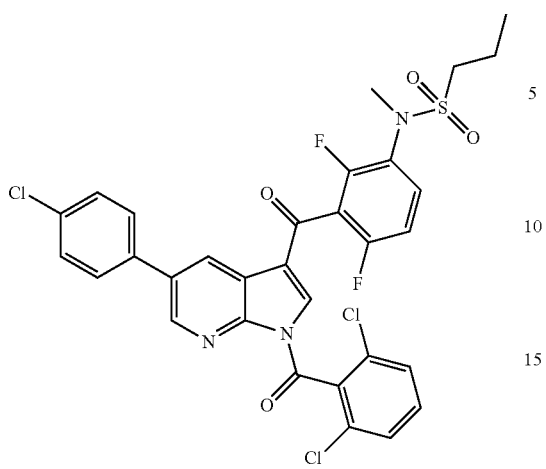

Propane-1-sulfonic acid{3-[5-(4-chloro-phenyl)-1-(2,6-dichloro-benzoyl)-1H-pyrrolo[2,3-b]pyridine-3-carbonyl]-2,4-difluoro-phenyl}-amide (0.5 g, 0.8 mmol) were dissolved in 1 ml dimethylformamide 0.1 g sodium carbonate was added under stirring at room temperature. Methyl iodide (70 µl, 0.16 g, 1.1 mmol) was added dropwise under vigorous stirring at room temperature by a syringe. The reaction mixture was stirred at room temperature overnight. Water was added to the stirred suspension, and the mixture was stirred for 1 hour. The reaction mixture was extracted with ethyl acetate twice (2×20 ml). The organic layer was dried over sodium sulfate. After drying of the organic layer, the solvent was evaporated under reduced pressure at 46° C. The brownish remaining crude product was used for the further synthesis without purification.

Yield: 0.50 g (0.74 mmol); 98% of theoretical yield.
Purity 93.59% (at 254.4 nm) (method A)
LC-MS: Retention time: 12.002 min.; m/z: 676.4

Step 2: Preparation of N-methyl Vemurafenib ("Compound 2")

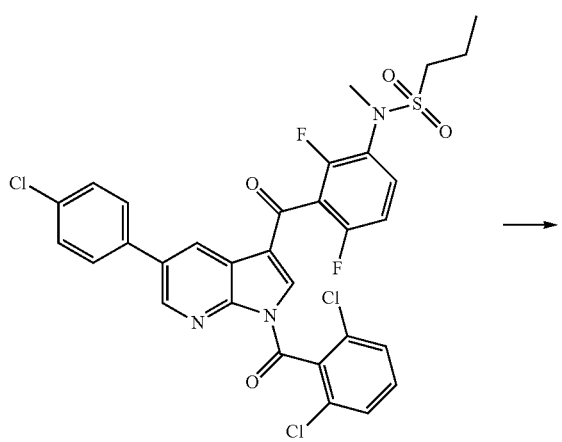

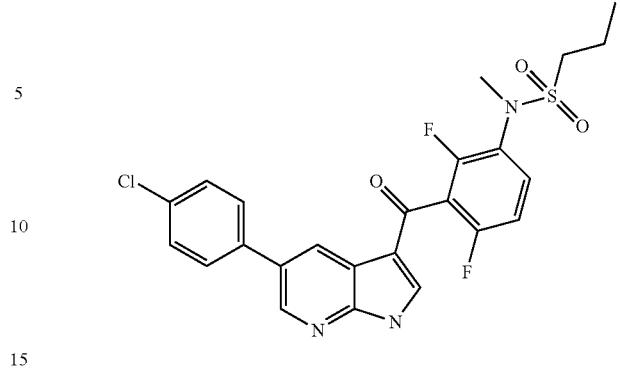

Propane-1-sulfonic acid{3-[5-(4-chloro-phenyl)-1-(2,6-dichloro-benzoyl)-1H-pyrrolo[2,3-b]pyridine-3-carbonyl]-2,4-difluoro-phenyl}-methyl-amide (0.5 g, 0.7 mmol) was dissolved in 1 ml DMF and 0.8 ml methanol at RT. 15% ammonia in methanol were added and the mixture was heated to 50-55° C. under stirring for 18 h. The clear solution was concentrated under reduced pressure at 43°. Methanol (20 ml) added to the mixture was evaporated again under reduced pressure at 43° C. The obtained residue was subjected to flash chromatography (silica; eluent: ethyl acetate/n-hexane 2/1). The product was obtained as a slightly brownish solid.

Yield: 0.21 g, (0.42 mmol)1 56% of theoretical yield.
Purity: 96.89% (254.4 nm) (method A)
LC-MS: Retention time 6.165 min; m/z 504.3
$^1$H NMR (400 MHz, ACETONE-$d_6$) δ ppm 1.03 (t, J=7.43 Hz) 1.84 (m, 2H) 3.20 (m, 2H) 3.32 (s, 3H) 7.23 (m, 1H) 7.40 (m, J=6.26, 6.26 Hz) 7.55 (d, J=8.60 Hz, 2H) 7.72 (m, 1H) 7.79 (d, J=8.60 Hz, 2H) 8.16 (s, 1H) 8.70 (d, J=2.35 Hz, 1H) 8.76 (s, 1H) 11.88 (s, 1H). A $^1$H NMR spectrum of compound 2 is shown in FIG. 11.
$^{13}$C NMR (100 MHz, ACETONE-$d_6$) δ ppm 12.3, 16.9, 37.7, 52.2, 63.3, 112.2, 112.4, 116.7, 117.8, 127.7, 128.0, 129.0, 129.1, 130.4, 131.1, 132.8, 132.9, 133.2, 137.5, 137.7, 144.3, 149.2, 157.1, 157.4, 159.6, 177.2, 180.4, 204.1. A $^{13}$C NMR spectrum of compound 2 is shown in FIG. 12.
IR (ATR) [cm$^{-1}$]: 3095, 2981, 2840, 1617, 1592, 1474, 1416, 1332, 1255, 1162, 1138, 1097, 1014, 953, 912, 862, 821, 791, 652. An IR spectrum of compound 2 is shown in FIG. 13.

What is claimed is:
1. A crystalline Vemurafenib choline salt designated as Form C1 and characterized by
   a powder XRD pattern with peaks at 7.9, 12.4, 13.8, 19.2 and 20.6 degrees 2-theta±0.2 degrees 2 theta and one or more of the following;
   a powder XRD pattern as shown in FIG. 8;
   a solid state 13C NMR spectrum having chemical shift differences between said characteristic peaks and a peak at 149.5 ppm±0.2 ppm of –13.2, –30.1, –33.2, –93.3 and –95.9 ppm±0.1 ppm, respectively;
   a solid state 13C NMR spectrum substantially as shown in FIG. 16;
   and combinations of these data.
2. The Vemurafenib choline salt of claim 1 wherein the molar ratio between Vemurafenib and choline is about 1:1.
3. The crystalline form of claim 1, further characterized by any one, two, three, four or five additional powder XRD peaks selected from the group consisting of: 13.0, 14.1, 16.0, 16.3 and 16.6 degrees 2-theta±0.2 degrees 2-theta.
4. The crystalline form of claim 1, characterized by a DSC thermogram substantially as shown in FIG. 9.

5. The crystalline form of claim 1, wherein the crystalline form is an anhydrous form.

6. A pharmaceutical composition comprising the crystalline Vemurafenib choline salt according to claim 1.

7. A pharmaceutical formulation comprising the crystalline Vemurafenib choline salt according to claim 1, and at least one pharmaceutically acceptable excipient.

8. A process for preparing the pharmaceutical formulation according to claim 7 comprising combining the crystalline Vemurafenib choline salt according to claim 1 with at least one pharmaceutically acceptable excipient.

9. A method of treating a subject suffering from melanoma, comprising administering to the subject a therapeutically effective amount of the crystalline Vemurafenib choline salt according to claim 1, the pharmaceutical composition according to claim 6, or the pharmaceutical formulation according to claim 7.

\* \* \* \* \*